United States Patent [19]

Kassis

[11] Patent Number: 5,443,447
[45] Date of Patent: Aug. 22, 1995

[54] INTRACAVITARY DELIVERY OR WITHDRAWAL DEVICE

[75] Inventor: Amin I. Kassis, 28 South St., Chestnut Hill, Mass. 02167

[73] Assignee: Amin I. Kassis, Boston, Mass.

[21] Appl. No.: 212,681

[22] Filed: Mar. 11, 1994

Related U.S. Application Data

[63] Continuation of Ser. No. 950,158, Sep. 24, 1992, abandoned.

[51] Int. Cl.⁶ .................................... A61M 29/00
[52] U.S. Cl. .................................... 604/96; 604/24
[58] Field of Search ................... 604/24, 27, 26, 29, 604/30, 31–35, 41–43, 54, 55, 96; 128/200.11, 200.23

[56] References Cited

U.S. PATENT DOCUMENTS

| | | |
|---|---|---|
| 248,983 | 11/1881 | Beall . |
| 1,854,726 | 4/1932 | Ziegler . |
| 2,157,614 | 5/1939 | Lazarus . |
| 2,564,809 | 8/1951 | Levene . |
| 2,623,519 | 12/1952 | Cohen . |
| 3,024,787 | 3/1962 | Birch et al. . |
| 3,157,201 | 11/1964 | Littman ............................ 604/32 |
| 3,394,705 | 7/1968 | Abramson ........................ 604/43 |
| 3,470,869 | 10/1969 | Fenton et al. . |
| 3,678,959 | 7/1972 | Liposky ............................ 604/33 |
| 3,709,222 | 1/1973 | DeVries ............................ 604/29 |
| 3,780,736 | 12/1973 | Chen ................................ 604/32 |
| 4,090,502 | 5/1978 | Tajika . |
| 4,356,824 | 11/1982 | Vazquez . |
| 4,533,345 | 8/1985 | Louw ................................ 604/43 |
| 4,604,089 | 8/1986 | Santanyeb et al. .............. 604/30 |
| 4,619,247 | 10/1986 | Inoue ................................ 604/96 |
| 4,637,814 | 1/1987 | Leiboff ............................ 604/39 |
| 4,955,375 | 9/1990 | Martinez ........................ 604/280 |
| 4,962,868 | 10/1990 | Borchard ........................ 222/49 |
| 5,025,806 | 6/1991 | Palmer ........................ 128/203.12 |
| 5,062,423 | 11/1991 | Matson ........................ 128/207.15 |

Primary Examiner—Jerome L. Kruter
Attorney, Agent, or Firm—Banner & Allegretti, Ltd.

[57] ABSTRACT

An apparatus for the rapid delivery of therapeutic and or diagnostic agent to a body cavity or withdrawal of fluid from the body cavity is disclosed. This apparatus comprises in combination a catheter having a first and second conduit, an atomizer connected to the distal end of the first conduit, and a balloon surrounds the conduits. A multi-port valve is connected to the proximal end of the second conduit. An inflation tube with its input end connect to the multi-port valve while the output end connects to the balloon. A chamber for dispensing the selected agent is attached to one of the opening of multi-port valve via its air input while its output port is connected to the first conduit via a pressure relief membrane. A collection system having a three-way valve is connected to the opening of the multi-port valve by a third conduit.

23 Claims, 5 Drawing Sheets

INTRACAVITARY DELIVERY OR WITHDRAWAL DEVICE

This application is a continuation of application Ser. No. 07/950,158 filed Sep. 24, 1992, mow abandoned.

FIELD OF THE INVENTION

This invention relates to a method for the delivery of therapeutic or diagnostic agents, as well as apparatus therefor, and more particularly it relates to a method and apparatus for rapidly delivering a high concentration of atomized therapeutic or diagnostic agent to the surface of a cavity. It also includes within its scope a method and apparatus for the withdrawal of body fluid from a body cavity.

BACKGROUND OF THE INVENTION

U.S. Pat. No. 3,394,705 issued to Abramson teaches a catheter for fine spray irrigation of antiseptics and antibiotics in the region of the urethra immediately adjacent to the bladder. The catheter comprises a small diameter tube for passing entirely through the urethra, an inflatable bag for seating within the bladder, and an antiseptic fluid chamber with small apertures encircling the tube for fine spray irrigation. The small apertures are uniformly spaced in a spiral so that irrigation and drainage through them will be uniform.

U.S. Pat. No. 4,533,345 issued to Louw teaches a catheter of flexible construction for treating the human uterus. The catheter possesses sufficient stiffness to permit introduction into the body by itself without the need for a rigid stiffening device. The catheter is combined with a means for flushing or introducing medication through radial spray holes.

U.S. Pat. No. 4,619,247 issued to Inoue et al. teaches a catheter or fiberscope apparatus for inspection of intracavitary areas like the heart. The catheter comprises a flexible tube divided into four passageways with a balloon mounted on its end. The flexible tube is constructed with two fluid passageways, an illumination light transmission line, and an image transmission line. The use of a physiological saline spray dispensed from one fluid passageway outside of the balloon for the purpose of flushing the area to be inspected to remove obstructing materials from the field through which light rays pass and to prevent direct contact between the balloon and the area to be inspected is taught.

U.S. Pat. No. 4,955,375 issued to Martinez teaches a catheter or endotracheal tube combined with a means for administering medication. The catheter comprises a channel formed by a flexible elastic wall attached to an inner wall of the catheter with a flared portion at the distal end. When medication is introduced into the channel, pressure due to ventilating air compresses the channel, forcing the medication to the flared portion where it is atomized.

U.S. Pat. No. 4,962,868 issued to Borchard teaches an apparatus for administering a controlled dose of a liquid medication to each nostril of the nose. The apparatus comprises a syringe completely encased in a tube, a piston connected to the plunger end of the syringe, and an atomizer head fitted over the needle end of the syringe. When the plunger is depressed, the liquid in the syringe is atomized and administered to the nostrils.

U.S. Pat. No. 5,025,806 issued to Palmer et al. teaches a ventilating/aspirating apparatus for introducing medication into the lungs of a patient without the need for disconnecting breathing apparatus or interrupting the ventilation or aspiration cycle. A metered predetermined dosage of medication is introduced as an atomized spray into the respirating system of the patient during artificial ventilation, aspiration, and when neither ventilation nor aspiration is occurring. The atomized medication is dispensed from a pressurized container with a manually activated normally closed valve during the respiration cycle or between the respiration and aspiration cycles.

U.S. Pat. No. 5,062,423 issued to Matson et al. teaches a method of and apparatus for delivering a dose of an aerosol drug to the lungs of a large animal. An endotracheal-like nasal tube is inserted through the nostril of the large animal and an aerosol drug dose is discharged into the lumen of the nasal tube. The inwardly flowing air carries the atomized drug dose with it for delivery to the lungs of the large animal.

There still remains a need for an intracavitary therapeutic or diagnostic agent atomizer capable of rapidly depositing, in higher concentration than devices known in the art, precious or radioactive therapeutic or diagnostic agents with a relatively small drug volume no or minimal excess. Moreover, there remains a need for an intracavitary drug atomizer that contains the used therapeutic or diagnostic products.

SUMMARY OF THE INVENTION

It is an object of this invention to allow rapid delivery of a high concentration of atomized therapeutic or diagnostic agent to the surface of any cavity within a human or animal body.

It is a further object of the invention to deliver a radioactive therapeutic or diagnostic agent to the surface of any cavity within a human or animal body with a relatively small source therapeutic or diagnostic agent volume.

It is yet another object of the invention to contain any resulting used products.

The present invention takes the form of a method and apparatus for delivering an atomized therapeutic or diagnostic agent to the surface of a cavity within a human or animal body.

These objects, features, and advantages of the present invention will become more apparent through a consideration of the following detailed description including a preferred embodiment of the invention. In the course of this description, reference will frequently be made to the attached drawings.

BRIEF DESCRIPTION OF THE DRAWINGS

The invention will be further described with reference to the drawing wherein.

DETAILED DESCRIPTION

Figure 1:
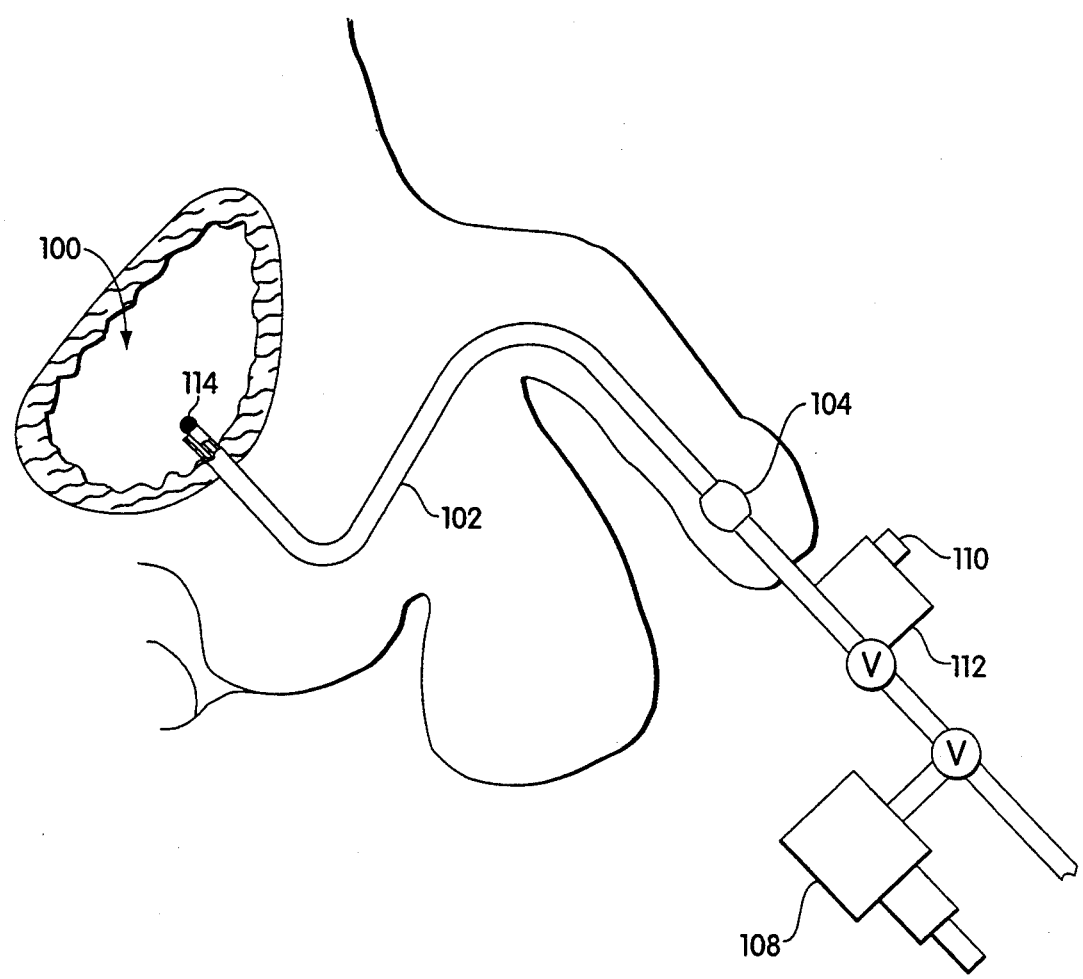
FIG. 1 is a schematic illustration of one embodiment of an atomizer apparatus in accordance with the present invention.
Figure 2:
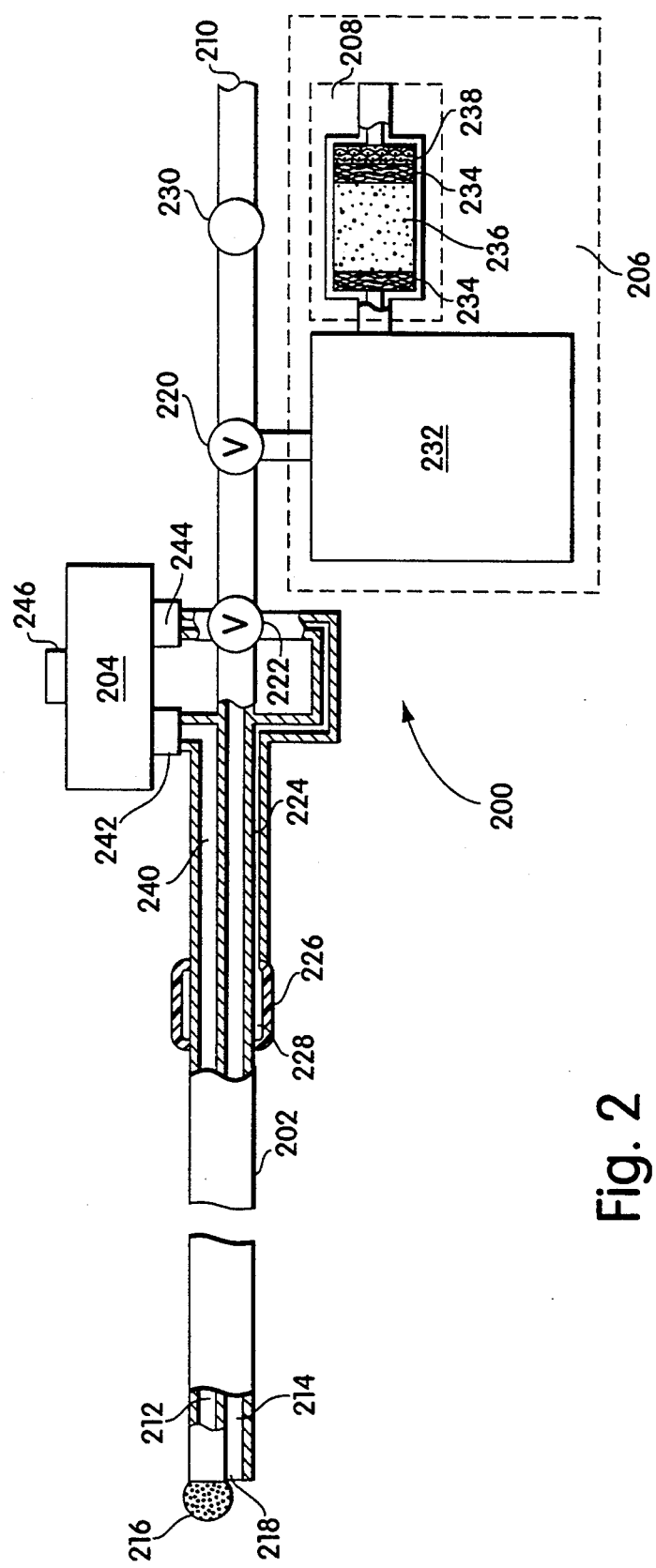
FIG. 2 is a schematic illustration of one embodiment of an atomizer apparatus in accordance with the present invention.

Referring now to FIG. 1, it shows a method as well as an apparatus useful for administering a therapeutic or diagnostic agent to the interior walls of a body cavity, such as a human bladder cavity which is indicated generally at 100. A flexible catheter indicated generally at 102 that is typically up to several mm in diameter is inserted into a body passageway like the urethra and snaked into the body cavity 100. The exterior surface of the catheter is typically made of nylon or any other inert material such as polyvinyl chloride, and the like and optionally coated with silicone or teflon.

Once within the body cavity 100, a balloon 104 in the shape of a donut that circumscribes the catheter is inflated at a predetermined distance from the tip of the catheter with a pressurized gas such as carbon dioxide. The balloon secures and positions the catheter tightly against the body passageway advantageously forming a gas-tight seal thereby blocking the passage of material through the passageway exterior to the catheter.

In a preferred embodiment of this invention, the fluid in the body cavity 100 is drained through the catheter 102 into a liquid collection vessel 108. This method can be used for the purpose of preparing the body cavity 100 for accepting the diagnostic or therapeutic agent and for analyzing the body fluid within the body cavity 100.

To prepare the body cavity 100 for accepting the diagnostic or therapeutic agent, the body cavity 100 is inflated by administering a pressurized gas through the catheter 102 into the body cavity 100.

A therapeutic or diagnostic agent dissolved or suspended in a physiologically acceptable carrier, e.g. normal saline, is administered through an inlet port 110 into a chamber 112. The carrier is forced under pressure through an atomizer 114 where it advantageously forms a directed spray into the body cavity thereby coating the interior walls of the cavity 100 with the therapeutic or diagnostic agent in a concentration and amount sufficient to coat the entire area of the interior wall with no or minimal excess.

Once the interior walls of the body cavity 100 are sufficiently coated, the body cavity 100 is deflated by allowing the pressurized gas to escape through the catheter 102. Finally, the balloon 104 is deflated and the catheter 102 is removed from the body passageway.

The method of this embodiment is particularly advantageous for use in dispensing radioactive or precious drugs because the expense or radiation exposure of non-target tissues in the patient and surrounding medical staff will be greatly reduced. For example, if the cells within a human bladder cavity are to be exposed to 1 mg/ml of a certain drug, a 1 ml solution containing 1 mg of the drug can be atomized and evenly spread on the inside surface of the bladder cavity. To achieve a similar exposure in a human bladder cavity with a liquid application, it will be necessary to dissolve 500 mg of the drug in 500 ml of the solution.

An apparatus that may be employed to perform the method of the invention is designated in its entirety by the reference numeral 200 as illustrated in FIG. 2. The apparatus 200 generally comprises a catheter 202, a chamber 204, a liquid collection system 206, a two-port filter system 208, and a gas/liquid inlet 210.

The catheter 202 comprises a first 212 and second 214 conduit. The distal end of the first conduit is terminated by one or more atomizers 216 that directs an agent spray into a body cavity. The distal end of the second conduit is terminated by an aperture 218 that allows air and fluid to freely pass through in both directions.

A three-way valve 220 and a four-way valve 222 connect the gas/liquid inlet 210 to the second conduit 214, to the inflation tube 224, and to the chamber 204. The three-way valve 220 also connects the liquid collection bottle 232 to the gas/liquid inlet 210.

A balloon 226 surrounds the outer surface of the catheter 202 near the proximal end of the catheter 202. An inflation tube 224 with its input connected to the four-way valve 222 and its output sealed within the inner surface of the balloon 228 is advantageously used to inflate the balloon 226. When properly configured, the four-way valve 222 advantageously permits a pressurized gas such as carbon dioxide to flow through the inflation tube 224 and thereby inflate the balloon 228 advantageously forming a gas-tight seal. The gas flow is preferably controlled by a pressure regulator 230. This entire procedure blocks the passage of material through the passageway exterior to the catheter.

In a preferred embodiment of this invention, the body cavity 100 is drained by configuring the three-way 220 and four-way 222 valves to permit any liquid within the body cavity to flow through the second conduit 214 and into the collection bottle 232. The body cavity 100 is inflated by configuring the three-way 220 and four-way 222 valves to permit the pressurized gas to flow through the second conduit 214 and into the body cavity 100.

The chamber 204 in the preferred embodiment is attached to the proximal end of the first conduit 240 by a pressure relief membrane or one-way valve 242 and to the four-way valve 222 by a gas pressure relief membrane or one-way valve 244. The chamber 204 comprises an inlet port 246 for introducing therapeutic or diagnostic agents.

In the preferred embodiment of this invention, the inlet port 246 accepts a therapeutic or diagnostic agent dissolved or suspended in a physiologically acceptable carrier into the chamber 204. When properly configured, the three-way 220 and four-way 222 valves permit a pressurized gas such as carbon dioxide to flow from the gas/liquid 210 inlet into contact with the gas pressure relief membrane or one-way valve 244. When the gas pressure exceeds the rupture/release threshold of the gas/liquid pressure relief membrane or one-way valve 244, the membrane bursts advantageously pressurizing the chamber 204. When the pressure inside the chamber exceeds the rupture threshold of the pressure relief membrane or one-way valve 242, the membrane/-valve 242 bursts thereby forcing the therapeutic or diagnostic agent under pressure through the atomizing aperture 216.

In the preferred embodiment of this invention, the rupture thresholds of the gas pressure relief membrane or one-way valve 244 and the pressure relief membrane or one-way valve 242 are not necessarily equal. The minimum pressure at which the liquid carrier approaches the atomizer 216 is controlled by the rupture threshold of the pressure relief membrane or one-way valve 242. Accordingly, this threshold is adjusted for different applications. For example, an application requiring coating the inside of a large cavity may require a pressure relief membrane with a large rupture threshold. The interaction time necessary to completely atomize the liquid carrier may depend on its viscosity. Accordingly, this threshold is adjusted to match the viscosity of the liquid carrier.

After applying the therapeutic or diagnostic agent to interior walls of the body cavity 100, the three-way 220 and four-way 222 valves will be configured such that the liquid and gas in the gas-inflated body cavity 100 can escape into the liquid collection vessel 232 thus deflating the cavity. The displaced pressurized gas is passed from the liquid collection vessel 232 through a filter 208 suitable for preventing the airborne passage of contaminants into the surrounding environment. The filter 208 in the preferred embodiment contains cotton 234 to trap any moisture or liquid droplets, charcoal 236 to trap certain radioactive atoms or molecules when such compounds are being used, and a fine mesh filter 238 such as a membrane filter available from Millipore Filter Corporation of Bedford, Mass. to trap any microorganisms.

After draining the body cavity, the three-way 220 and four-way 222 valves are configured such that the balloon 226 is allowed to deflate. The catheter 202 can then be removed from the body cavity 100.

Figure 3:
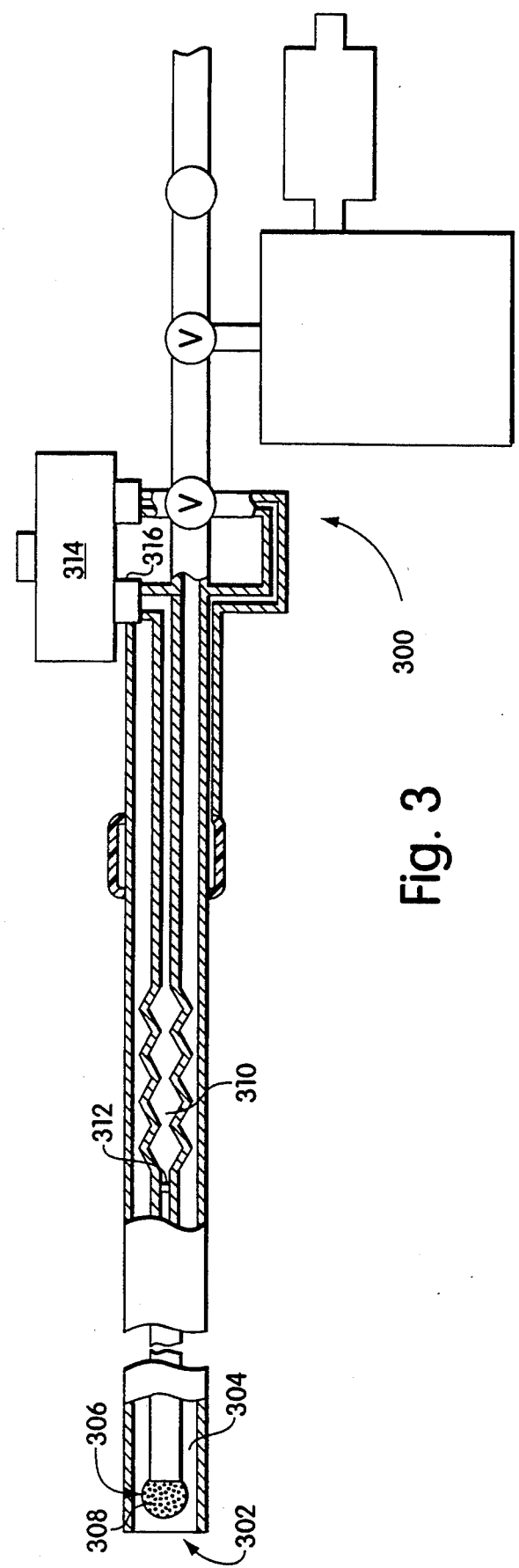
FIG. 3 is a schematic illustration of an alternative embodiment of an atomizer apparatus in accordance with the present invention.

An alternate apparatus that may be employed to perform the method of the invention is designated in its entirety by the reference numeral 300 as illustrated in FIG. 3. The alternate apparatus 300 additionally utilizes a method wherein the distal end of the catheter 302 is mounted within a protective shield comprising the second conduit 304. This method is advantageous because it isolates the atomizer 306 from bodily substances during catheter insertion and thereby protects the fine spray holes 308 from potentially being obstructed by bodily fluids.

In the preferred embodiment of the alternate apparatus 300, the first conduit comprises a bellows 310 with one end flexible connected to the atomizer 306 by a bellows relief membrane or one-way valve 312 and the other end flexibly connected to chamber 314 by a pressure relief membrane or one-way valve 316. The rupture threshold pressure of the bellows pressure membrane or one-way valve 312 is specifically designed to be greater than the rupture threshold pressure required to burst/open the pressure relief membrane 316.

When the pressure relief membrane/one-way valve 316 bursts/opens, the bellows 310 pressurizes and thereby straightens. The resulting motion translates the atomizer 306 beyond the protective sheath comprising the second conduit 304 into the gas filled body cavity 100. At this point, the bellows pressure membrane/one-way valve 312 will rupture/open and the therapeutic or diagnostic agent will be delivered via the atomizer 306 into the body cavity 100.

Figure 4:
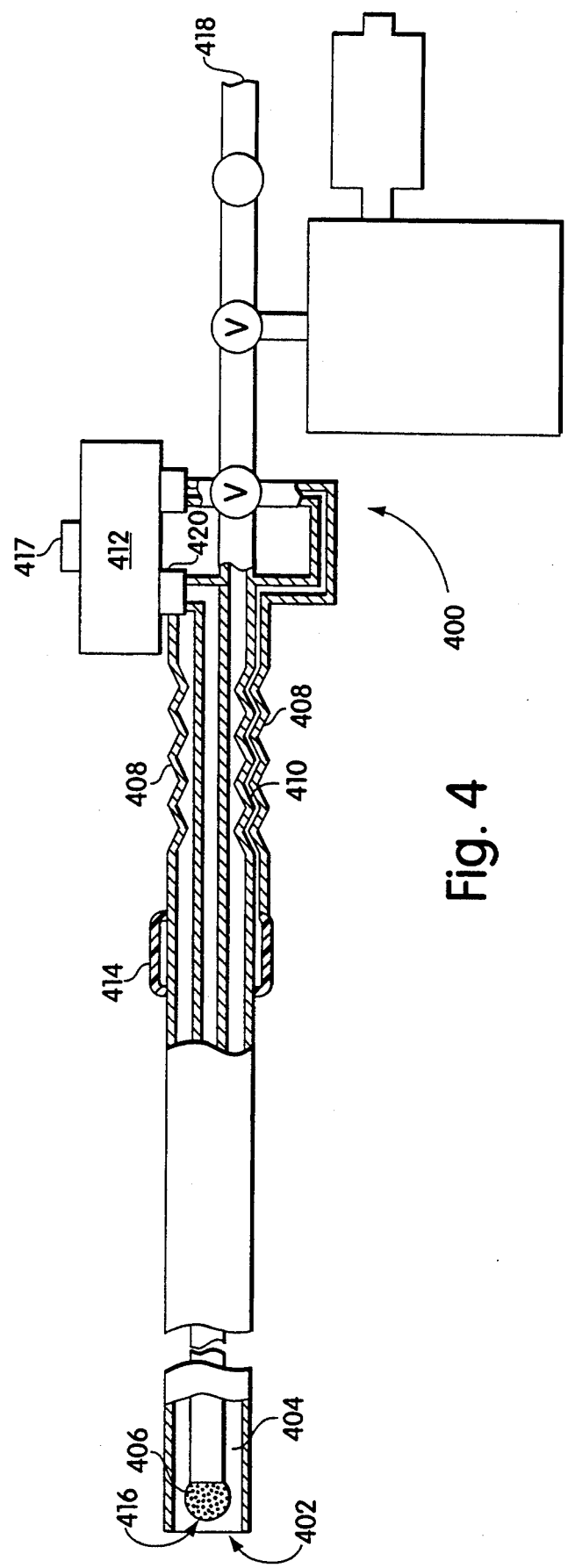
FIG. 4 is a schematic illustration of a further alternative embodiment of an atomizer apparatus in accordance with the present invention.

A further alternate apparatus that may be employed to perform the method of the invention is designated in its entirety by the reference numeral 400 as illustrated in FIG. 4. The alternate apparatus 400 additionally utilizes a further method wherein the distal end of the catheter 402 is mounted within a retractable protective shield comprising the second conduit 404. This method is also advantageous because it isolates the atomizer from bodily substances during catheter insertion and thereby protects the fine spray holes 406 from potentially obstructing bodily fluids.

In a preferred embodiment of this alternate apparatus 400, the outside of the second conduit 408 and the inflation tube 410 comprises a compressible bellows located between the chamber 412 and the balloon 414. The method employed in implementing this preferred embodiment comprises the steps of manually holding, preferably with the thumb and forefinger of one hand, the proximal end of the catheter between the bellows 408, 410 and the balloon 414. The apparatus 400 is preferably held with the second hand at, for example, the chamber 412. The second hand pushes forward towards the distal end of the catheter 402 compressing the bellows 408, 410 thereby translating the atomizer 416 beyond the protective sheath comprising the second conduit 404 into the gas filled body cavity 100. The therapeutic or diagnostic agent that had been introduced from the inlet port 417 in the chamber 412, is injected with a pulse of gas delivered from the gas/liquid inlet 418. When the pressure inside the chamber exceeds the rupture/open threshold of the pressure relief membrane/one-way valve 420, the membrane/valve yields to the pressure and ruptures/opens thereby forcing the therapeutic or diagnostic agent under pressure through the atomizing aperture 416 into the body cavity 100.

Figure 5:
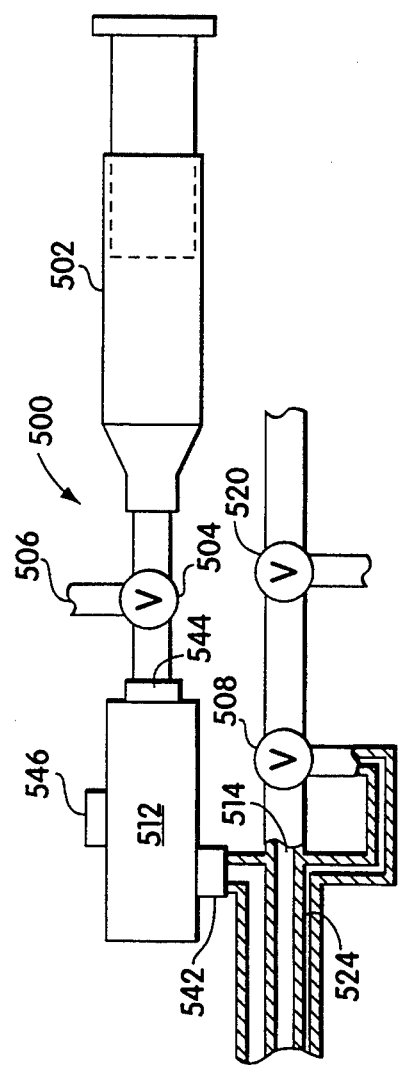
FIG. 5 is a schematic illustration of an alternative embodiment of injecting the therapeutic or diagnostic agent into the atomizer apparatus in accordance with the present invention.

An alternate apparatus that may be employed to perform the method of introducing the therapeutic or diagnostic agent into the body cavity 100 is designated in its entirety by the reference numeral 500 as illustrated in FIG. 5. The alternate apparatus 500 utilizes a syringe 502 to dispense the therapeutic or diagnostic agent from within chamber 512 into the body cavity 100. In this embodiment of this invention, the inlet port 546 accepts a therapeutic or diagnostic agent dissolved or suspended in a physiologically acceptable carrier into the chamber 512. When properly configured, the three-way 504 valve permits a pressurized gas such as carbon dioxide that is present within syringe 502 to flow from the syringe 502 into contact with the gas pressure relief membrane or one-way valve 544. When the gas pressure exceeds the rupture/release threshold of the gas/liquid pressure relief membrane or one-way valve 544, the membrane bursts advantageously pressurizing the chamber 512. When the pressure inside the chamber exceeds the rupture threshold of the pressure relief membrane or one-way valve 542, the membrane/valve 542 bursts thereby forcing the therapeutic or diagnostic agent under pressure through the atomizing aperture 216. The syringe 502 is connected to the pressure relief membrane or one-way valve 544 through a three-way valve 504. A gas inlet 506 is also connected to the three-way valve 504. In this apparatus 500, a three-way valve 508 connects the second conduit 514, the inflation tube 524, and the three-way valve 520.

It is to be understood that the specific methods and apparatuses which have been described are merely illustrative of an application of the principles of the invention. The bladder was used to depict a well defined cavity within a human, but the methods and apparatus described apply to any other cavity, natural or man made (for example, a cavity resulting from a tumor resection), within a human or animal.

What is claimed is:

1. In combination,
    a catheter comprising, in combination,
        a first and second conduit each with an aperture at its distal and proximal end,
        an atomizer flexibly connected to the distal end of the first conduit,
        a balloon surrounding the conduits,
        a multi-port valve operatively connected to the proximal end of said second conduit, and an inflation tube with its input in fluid communication with said multi-port valve and its output in fluid communication with said balloon, a chamber for introducing a fluid agent comprising, in combination, a fluid input operatively connected to said multi-port valve through a first valve means for delivery of pressurized fluid flow, a chamber inlet port, and an output operatively connected to the proximal end of said first conduit by a second valve means for delivery of pressurized fluid flow, a collection system comprising a three-way valve operatively connected to said multi-port valve by a third conduit and a vessel comprising an input port operatively connected to said three-way valve and a gas exhaust port, a two-port filter system with one end operatively connected to said gas exhaust port, and a gas/liquid inlet operatively connected to said three-way valve comprising a fourth conduit with a means for controlling flow rate.

2. A combination as set forth in claim 1 wherein said multiport valve is a four-way valve.

3. A combination as set forth in claim 1 wherein said first conduit is retractable within said second conduit and said first conduit comprises, in combination, said atomizer flexibly connected to a third valve means for delivery of pressurized fluid flow, and a bellows with its first end operatively connected to said third valve means and its second end flexibly connected to said chamber.

4. A combination as set forth in claim 1 wherein the distal end of said first conduit and said inflation tube comprises a compressible bellows located between said chamber and said balloon and said conduit is retractable to a position beyond the end of said atomizer.

5. A combination as set forth in claim 1 wherein said multi-port valve is a three-way valve and wherein said chamber for introducing a fluid agent comprises, in combination, a fluid input operatively connected to a chamber three-way valve through a pressure relief membrane or one-way valve, a syringe operatively connected to said chamber three-way valve, a gas inlet operatively connected to said chamber three-way valve, and an output operatively connected to the proximal end of said first conduit by a pressure relief membrane or one-way valve.

6. A combination as set forth in claim 3 wherein said multi-port valve is a three-way valve and wherein said chamber for introducing a fluid agent comprises, in combination, a fluid input operatively connected to a chamber three-way valve through a pressure relief membrane or one-way valve, a syringe operatively connected to said chamber three-way valve, a gas inlet operatively connected to said chamber three-way valve, and an output operatively connected to the proximal end of said first conduit by a pressure relief membrane or one-way valve.

7. A combination as set forth in claim 4 wherein said multiport valve is a three-way valve and wherein said chamber for introducing a fluid agent comprises, in combination, a fluid input operatively connected to a chamber three-way valve through a pressure relief membrane or one-way valve, a syringe operatively connected to said chamber three-way valve, a gas inlet operatively connected to said chamber three-way valve, and an output operatively connected to the proximal end of said first conduit by a pressure relief membrane or one-way valve.

8. A combination as set forth in claim 1 wherein said two-port filter system comprises, in combination, a first cotton filter section operatively connected to said gas exhaust port, a charcoal filter section operatively connected to said first cotton filter section, a second cotton filter section operatively connected to said charcoal filter section, a fine mesh filter section operatively connected to said second cotton filter section, and a gas exhaust port operatively connected to said fine mesh filter section.

9. A catheter as set forth in claim 1 having an exterior surface being nylon polyethylene or poly vinyl chloride.

10. A combination as set forth in claim 1 wherein said means for controlling flow rate comprises a gas/liquid flow meter.

11. A combination as described in claim 1 with said vessel containing a tube operatively connected to said three-way valve.

12. An intracavitary delivery system comprising, in combination, a catheter for insertion into a body cavity comprising a first and second conduit;

the first conduit having a distal end and a proximal end, the distal end being operatively connected to a means for discharging a fluid agent in an atomized form and the proximal end being operatively connected to a chamber means for housing the fluid agent;

the second conduit having a distal end and a proximal end, the distal end comprising an aperture and the proximal end being operatively connected to a first vessel means for receiving cavitary fluid from the body cavity;

seal means for sealing the catheter against the interior of the body cavity, the seal means being inflatable and fixedly circumscribing the catheter at a predetermined distance away from the distal end;

means for generating a pressurized gas being operatively connected to the chamber means, the second conduit and the seal means;

a plurality of valve means for delivery of pressurized fluid flow, a first valve means disposed between the first conduit and the chamber means, a second valve means disposed between the chamber means and the means for generating a pressurized gas, a third valve means disposed between the means for generating a pressurized as and the second conduit, a fourth valve means disposed between the means for generating a pressurized gas and the seal means, and a fifth valve means disposed between the second conduit and the first vessel means.

13. The intracavitary delivery system of claim 12 wherein the first and second valve means open in response to a predetermined pressure level.

14. The intracavitary delivery system of claim 13 further comprising a filter means for filtering pressurized gas relieved from the body cavity, the filter means being operatively connected to the first vessel means.

15. The intracavitary delivery system of claim 14 wherein the means for discharging a fluid agent in an atomized form resides within the second conduit in concentric fashion to prevent unwanted matter from contacting the means for discharging a fluid agent in an atomized form, the first conduit being extendable so as to extend the means for discharging a fluid agent in an atomized form beyond the aperture of the second conduit.

16. The intracavitary delivery system of claim 14 wherein the means for discharging a fluid agent in an atomized form resides within the second conduit in concentric fashion to prevent unwanted matter from contacting the means for discharging a fluid agent in an atomized form, the second conduit comprising a retractable sheath so as to expose the means for discharging a fluid agent in an atomized form beyond the aperture of the second conduit.

17. The intracavitary delivery system of claim 14 wherein the means for generating a pressurized gas is a syringe.

18. An intracavitary delivery system comprising, in combination,
- a catheter for insertion into a body cavity having an access passageway comprising a first and second conduit;
- the first conduit having a distal end and a proximal end, the distal end being in fluid communication with a means for discharging a fluid agent in an atomized form and the proximal end being in fluid communication with a chamber means for housing the fluid agent;
- the second conduit having a distal end and a proximal end, the distal end comprising an aperture and the proximal end being operatively connected to a first vessel means for receiving cavitary fluid from the body cavity;
- seal means for sealing the catheter against the interior of the access passageway, the seal means being inflatable and fixedly circumscribing the catheter at a predetermined distance away from the proximal end;
- means for generating a pressurized gas being operatively connected to the chamber means, the second conduit and the seal means;
- a plurality of valve means for delivery of pressurized fluid flow having a first valve means disposed between the first conduit and the chamber means, a second valve means disposed between the chamber means and the means for generating a pressurized gas, a third valve means disposed between the means for generating a pressurized gas and the second conduit, a fourth valve means disposed between the means for generating a pressurized gas and the seal means, and a fifth valve means disposed between the second conduit and the first vessel means.

19. The intracavitary delivery system of claim 18 wherein the first and second valve means open in response to a predetermined pressure level.

20. The intracavitary delivery system of claim 19 further comprising a filter means for filtering pressurized gas relieved from the body cavity, the filter means being operatively connected to the first vessel means.

21. The intracavitary delivery system of claim 20 wherein the means for discharging a fluid agent in an atomized form resides within the second conduit in concentric fashion to prevent unwanted matter from contacting the means for discharging a fluid agent in an atomized form, the first conduit being extendable so as to extend the means for discharging a fluid agent in an atomized form beyond the aperture of the second conduit.

22. The intracavitary delivery system of claim 20 wherein the means for discharging a fluid agent in an atomized form resides within the second conduit in concentric fashion to prevent unwanted matter from contacting the means for discharging a fluid agent in an atomized form, the second conduit comprising a retractable sheath so as to expose the means for discharging a fluid agent in an atomized form beyond the aperture of the second conduit.

23. The intracavitary delivery system of claim 20 wherein the means for generating a pressurized gas is a syringe.

* * * * *